(12) United States Patent
Jackson

(10) Patent No.: US 8,273,109 B2
(45) Date of Patent: *Sep. 25, 2012

(54) HELICAL WOUND MECHANICALLY INTERLOCKING MATING GUIDE AND ADVANCEMENT STRUCTURE

(76) Inventor: Roger P. Jackson, Prairie Village, KS (US)

( * ) Notice: Subject to any disclaimer, the term of this patent is extended or adjusted under 35 U.S.C. 154(b) by 1368 days.

This patent is subject to a terminal disclaimer.

(21) Appl. No.: 10/831,919

(22) Filed: Apr. 26, 2004

(65) Prior Publication Data

US 2004/0199164 A1 Oct. 7, 2004

Related U.S. Application Data

(63) Continuation of application No. 10/236,123, filed on Sep. 6, 2002, now Pat. No. 6,726,689.

(51) Int. Cl.
*A61B 17/70* (2006.01)

(52) U.S. Cl. ............ 606/273

(58) Field of Classification Search ......... 606/61, 606/73; 411/414, 416, 393; 403/362
See application file for complete search history.

(56) References Cited

U.S. PATENT DOCUMENTS

| 791,548 A | 6/1905 | Fischer |
|---|---|---|
| 1,300,275 A | 4/1919 | Johnson |
| 1,330,673 A | 2/1920 | Anderson |
| 2,083,092 A | 1/1936 | Richer |
| 2,201,087 A | 5/1940 | Hallowell |
| 2,239,352 A | 4/1941 | Cherry |
| 2,295,314 A | 9/1942 | Whitney |
| 2,537,029 A | 8/1946 | Cambern |
| 2,445,978 A | 7/1948 | Stellin |
| 2,532,815 A | 12/1950 | Kindsvatter |
| 2,553,337 A | 5/1951 | Shafer |
| 2,778,265 A | 1/1957 | Brown |
| 2,969,250 A | 1/1959 | Kull |
| 2,877,681 A | 3/1959 | Brown |
| 2,927,332 A | 3/1960 | Moore |
| 3,143,029 A | 8/1964 | Brown |
| D200,217 S | 2/1965 | Curtiss |
| 3,370,341 A | 2/1968 | Allsop |
| 3,498,174 A | 3/1970 | Schuster et al. |
| 3,584,667 A | 6/1971 | Reiland |
| 3,640,416 A | 2/1972 | Temple |
| 3,812,757 A | 5/1974 | Reiland |
| 3,963,322 A | 6/1976 | Cryctko |
| 4,103,422 A | 8/1978 | Weiss |
| 4,269,246 A | 5/1981 | Larson et al. |

(Continued)

FOREIGN PATENT DOCUMENTS

DE 3630863 3/1988

(Continued)

OTHER PUBLICATIONS

Translation of DE 298 10 798, May 2010.*

(Continued)

*Primary Examiner* — Alvin Stewart
*Assistant Examiner* — David Comstock
(74) *Attorney, Agent, or Firm* — John C. McMahon

(57) ABSTRACT

A structure including a pair of helically wound interlocking forms located on a cylindrical closure for an open headed medical implant and in a receiver between arms of the implant respectively. The interlocking forms each include overlapping gripping elements that engage mating elements during assembly to prevent radial splaying of arms of the implant.

2 Claims, 8 Drawing Sheets

U.S. PATENT DOCUMENTS

| | | |
|---|---|---|
| 4,373,754 A | 2/1983 | Bollfrass et al. |
| 4,482,500 A | 11/1984 | Lewellyn |
| 4,492,500 A | 1/1985 | Ewing |
| 4,506,917 A | 3/1985 | Hansen Arne |
| 4,577,448 A | 3/1986 | Howorth |
| 4,600,224 A | 7/1986 | Blose |
| 4,641,636 A | 2/1987 | Cotrel |
| 4,703,954 A | 11/1987 | Ortloff et al. |
| 4,707,001 A | 11/1987 | Johnson |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,838,264 A | 6/1989 | Bremer et al. |
| 4,850,775 A | 7/1989 | Lee |
| 4,946,458 A | 8/1990 | Harms et al. |
| 5,005,562 A | 4/1991 | Cotrel |
| 5,022,791 A | 6/1991 | Isler |
| 5,026,373 A | 6/1991 | Ray et al. |
| 5,067,955 A | 11/1991 | Cotrel |
| 5,073,074 A | 12/1991 | Corrigan et al. |
| 5,092,635 A | 3/1992 | DeLange et al. |
| 5,129,388 A | 7/1992 | Vignaud et al. |
| 5,147,360 A | 9/1992 | Dubousset |
| 5,154,719 A | 10/1992 | Cotrel |
| 5,176,483 A | 1/1993 | Baumann et al. |
| 5,207,678 A | 5/1993 | Harms et al. |
| 5,217,497 A | 6/1993 | Mehdian |
| 5,261,907 A | 11/1993 | Vignaud et al. |
| 5,261,912 A | 11/1993 | Frigg |
| 5,275,601 A | 1/1994 | Gogolewski et al. |
| 5,282,707 A | 2/1994 | Palm |
| 5,312,404 A | 5/1994 | Asher et al. |
| 5,321,901 A | 6/1994 | Kelly |
| 5,334,203 A | 8/1994 | Wagner |
| 5,346,493 A | 9/1994 | Stahurski et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,382,248 A | 1/1995 | Jacobson et al. |
| 5,385,583 A | 1/1995 | Cotrel |
| 5,387,212 A | 2/1995 | Yuan et al. |
| 5,395,371 A | 3/1995 | Miller et al. |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,487,742 A | 1/1996 | Cotrel |
| 5,496,321 A | 3/1996 | Puno et al. |
| 5,499,892 A | 3/1996 | Reed |
| 5,507,747 A | 4/1996 | Yuan et al. |
| 5,545,165 A | 8/1996 | Biedermann et al. |
| 5,554,157 A | 9/1996 | Errico et al. |
| 5,562,663 A | 10/1996 | Wisnewski et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,591,235 A | 1/1997 | Kuslich |
| 5,601,553 A | 2/1997 | Trebing et al. |
| 5,607,304 A | 3/1997 | Bailey et al. |
| 5,607,426 A | 3/1997 | Ralph et al. |
| 5,624,442 A | 4/1997 | Mellinger et al. |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,713,705 A | 2/1998 | Grunbichler |
| 5,713,898 A | 2/1998 | Stucker et al. |
| 5,716,356 A | 2/1998 | Biedermann et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,782,833 A | 7/1998 | Haider |
| 5,797,911 A | 8/1998 | Sherman |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| D407,302 S | 3/1999 | Lawson |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,944,465 A | 8/1999 | Janitzki |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,053,917 A | 4/2000 | Sherman et al. |
| 6,056,753 A | 5/2000 | Jackson |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,139,550 A | 10/2000 | Michelson |
| 6,143,032 A | 11/2000 | Schafer et al. |
| 6,146,383 A | 11/2000 | Studer et al. |
| 6,149,533 A | 11/2000 | Finn |
| 6,183,472 B1 | 2/2001 | Lutz |
| 6,187,005 B1 | 2/2001 | Brace et al. |
| 6,193,719 B1 | 2/2001 | Gournay et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,248,105 B1 | 6/2001 | Schlapfer et al. |
| 6,254,146 B1 | 7/2001 | Church |
| 6,254,602 B1 | 7/2001 | Justis |
| 6,261,039 B1 | 7/2001 | Reed |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger |
| 6,309,391 B1 | 10/2001 | Crandall et al. |
| 6,315,564 B1 | 11/2001 | Levisman |
| 6,322,108 B1 | 11/2001 | Riesselmann et al. |
| 6,331,179 B1 | 12/2001 | Freid et al. |

| | | |
|---|---|---|
| 6,349,794 B2 | 2/2002 | Spencer |
| 6,355,040 B1 | 3/2002 | Richelsoph et al. |
| RE37,665 E | 4/2002 | Ralph et al. |
| 6,368,321 B1 | 4/2002 | Jackson |
| 6,402,752 B2 | 6/2002 | Schaffler-Wachter et al. |
| 6,440,135 B2 | 8/2002 | Orbay et al. |
| 6,440,137 B1 | 8/2002 | Horvath et al. |
| 6,443,953 B1 | 9/2002 | Perra et al. |
| 6,451,021 B1 | 9/2002 | Ralph et al. |
| 6,454,772 B1 | 9/2002 | Jackson |
| 6,471,703 B1 | 10/2002 | Ashman |
| 6,471,705 B1 | 10/2002 | Biedermann et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,520,963 B1 | 2/2003 | McKinley |
| 6,527,804 B1 | 3/2003 | Gauchet et al. |
| 6,530,929 B1 | 3/2003 | Justis et al. |
| 6,533,786 B1 | 3/2003 | Needham et al. |
| 6,540,749 B2 | 4/2003 | Schäfer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,602,255 B1 | 8/2003 | Campbell |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 * | 4/2004 | Jackson .................. 606/266 |
| 6,716,247 B2 | 4/2004 | Michelson |
| 6,723,100 B2 | 4/2004 | Biedermann et al. |
| 6,726,689 B2 * | 4/2004 | Jackson .................. 606/916 |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,932,817 B2 | 8/2005 | Baynham et al. |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,306,606 B2 | 12/2007 | Sasing |
| 2001/0001119 A1 | 5/2001 | Lombardo |
| 2002/0026193 A1 | 2/2002 | Barker et al. |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133154 A1 | 9/2002 | Saint Martin |
| 2002/0133158 A1 | 9/2002 | Saint Martin |
| 2002/0203511 | 9/2002 | Wilson-MacDonald et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023243 A1 | 1/2003 | Biedermann et al. |
| 2003/0028191 A1 | 2/2003 | Shluzas |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172032 A1 | 9/2004 | Jackson |
| 2004/0176766 A1 | 9/2004 | Shluzas |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0049589 A1 | 3/2005 | Jackson |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096653 A1 | 5/2005 | Doubler |
| 2005/0107788 A1 | 5/2005 | Beaurain et al. |
| 2005/0113927 A1 | 5/2005 | Malek |
| 2005/0131404 A1 | 6/2005 | Mazda et al. |

| | | | | | | |
|---|---|---|---|---|---|---|
| 2005/0131413 | A1 | 6/2005 | O'Driscoll et al. | EP | 1634537 | 3/2006 |
| 2005/0149023 | A1 | 7/2005 | Ritland | FR | 2467312 | 4/1981 |
| 2005/0154389 | A1 | 7/2005 | Selover et al. | FR | 2729291 | 7/1996 |
| 2005/0154391 | A1 | 7/2005 | Doherty et al. | FR | 2796545 | 1/2001 |
| 2005/0159750 | A1 | 7/2005 | Doherty | FR | 2856578 | 6/2003 |
| 2005/0165400 | A1 | 7/2005 | Fernandez | FR | 2865373 | 1/2004 |
| 2005/0171540 | A1 | 8/2005 | Lim et al. | FR | 2865375 | 1/2004 |
| 2005/0187548 | A1 | 8/2005 | Butler et al. | FR | 2865377 | 1/2004 |
| 2005/0187555 | A1 | 8/2005 | Biedermann et al. | FR | 2857850 | 4/2004 |
| 2005/0192580 | A1 | 9/2005 | Dalton | FR | 2865378 | 10/2004 |
| 2005/0203516 | A1 | 9/2005 | Biedermann et al. | GB | 203508 | 9/1923 |
| 2005/0216003 | A1 | 9/2005 | Biedermann et al. | GB | 2082709 | 3/1982 |
| 2005/0228501 | A1 | 10/2005 | Miller et al. | GB | 2140523 | 11/1984 |
| 2005/0234450 | A1 | 10/2005 | Barker | GB | 9202745.8 | 4/1992 |
| 2005/0234451 | A1 | 10/2005 | Markworth | GB | 2365345 | 2/2002 |
| 2005/0234452 | A1 | 10/2005 | Malandain | JP | 9-504727 | 5/1997 |
| 2005/0240181 | A1 | 10/2005 | Boomer et al. | RU | 371359 | 8/1973 |
| 2005/0240183 | A1 | 10/2005 | Vaughan | SU | 371359 | 2/1993 |
| 2005/0251137 | A1 | 11/2005 | Ball | WO | WO 92/03100 | 5/1992 |
| 2005/0251141 | A1 | 11/2005 | Frigg et al. | WO | WO94/10927 | 5/1994 |
| 2005/0261687 | A1 | 11/2005 | Garamszegi et al. | WO | WO94/10944 | 5/1994 |
| 2005/0267474 | A1 | 12/2005 | Dalton | WO | WO 94/26191 | 11/1994 |
| 2005/0273099 | A1 | 12/2005 | Baccelli et al. | WO | WO95/35067 | 12/1995 |
| 2005/0273101 | A1 | 12/2005 | Schumacher | WO | WO96/06576 | 3/1996 |
| 2005/0277919 | A1 | 12/2005 | Slivka et al. | WO | WO96/28118 | 9/1996 |
| 2005/0277925 | A1 | 12/2005 | Mujwid | WO | WO97/14366 | 4/1997 |
| 2005/0277928 | A1 | 12/2005 | Boschert | WO | WO98/32386 | 7/1998 |
| 2005/0283152 | A1 | 12/2005 | Lindemann et al. | WO | WO01/49191 | 7/2001 |
| 2005/0283157 | A1 | 12/2005 | Coates et al. | WO | WO02/054966 | 7/2002 |
| 2005/0283238 | A1 | 12/2005 | Reiley | WO | WO03/068088 | 8/2003 |
| 2005/0288669 | A1 | 12/2005 | Abdou | WO | WO2004/021900 | 3/2004 |
| 2005/0288671 | A1 | 12/2005 | Yuan et al. | WO | WO2004/041100 | 5/2004 |
| 2005/0288673 | A1 | 12/2005 | Catbagan et al. | WO | WO2004/089245 | 10/2004 |
| 2006/0004357 | A1 | 1/2006 | Lee et al. | WO | WO2004/107997 | 12/2004 |
| 2006/0004359 | A1 | 1/2006 | Kramer et al. | WO | WO2005/000136 | 1/2005 |
| 2006/0004360 | A1 | 1/2006 | Kramer et al. | WO | WO2005/000137 | 1/2005 |
| 2006/0004363 | A1 | 1/2006 | Brockmeyer et al. | WO | WO2005/020829 | 3/2005 |
| 2006/0009769 | A1 | 1/2006 | Lieberman | WO | WO2005/072632 | 8/2005 |
| 2006/0009770 | A1 | 1/2006 | Speirs et al. | WO | WO2005/082262 | 9/2005 |
| 2006/0015104 | A1 | 1/2006 | Dalton | WO | WO2005/099400 | 10/2005 |
| 2006/0025767 | A1 | 2/2006 | Khalili | WO | WO2006/012088 | 2/2006 |
| 2006/0025768 | A1 | 2/2006 | Iott et al. | WO | WO2006/017616 | 2/2006 |
| 2006/0025770 | A1 | 2/2006 | Schlapfer et al. | WO | WO2006/028537 | 3/2006 |
| 2006/0036242 | A1 | 2/2006 | Nilsson et al. | | | |
| 2006/0036252 | A1 | 2/2006 | Baynham et al. | | | |
| 2006/0052783 | A1 | 3/2006 | Dant et al. | | | |
| 2006/0052784 | A1 | 3/2006 | Dant et al. | | | |
| 2006/0052786 | A1 | 3/2006 | Dant et al. | | | |
| 2006/0058788 | A1 | 3/2006 | Hammer et al. | | | |

FOREIGN PATENT DOCUMENTS

| | | |
|---|---|---|
| DE | 373809 | 5/1989 |
| DE | 4425392 | 11/1995 |
| DE | 19507141 | 9/1996 |
| DE | 19509331 | 9/1996 |
| DE | 28910798 | 12/1999 |
| DE | 29810798 | 12/1999 |
| DE | 19951145 | 5/2001 |
| DE | 10157969 | 2/2003 |
| EP | 195455 | 9/1986 |
| EP | 172130 | 2/1987 |
| EP | 0276153 | 7/1988 |
| EP | 276153 | 7/1988 |
| EP | 465158 | 1/1992 |
| EP | 0885598 | 12/1998 |
| EP | 1090595 | 4/2001 |
| EP | 1121902 | 8/2001 |
| EP | 1190678 | 3/2002 |
| EP | 1210914 | 6/2002 |
| EP | 1277444 | 1/2003 |
| EP | 1449486 | 8/2004 |
| EP | 1570795 | 9/2005 |
| EP | 1579816 | 9/2005 |

OTHER PUBLICATIONS

*Spine*, Lipcott, Williams & Wilkins, Inc. vol. 24, No. 15, p. 1495, Aug. 1, 1999.
Brochure of Tyco/Healthcare/Surgical Dynamics on Spiral Radius 90D, Publication Date: Sep. 2001, pp. 1-8.
CD Horizon M8 Multi Axial Screw Spinal System Brochure, Medtronic Sofamor Danek, no publish date.
EBI Omega 21 Brochure, EBI Spine Systems, pub. 1999.
SDRS Surgical Dynamics Rod System Brochure, Surgical Dynamics, pub. 1998-1999.
Silhouette Spinal Fixation System Brochure, Sulzer Medica SpineTech, no publish date.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.

* cited by examiner

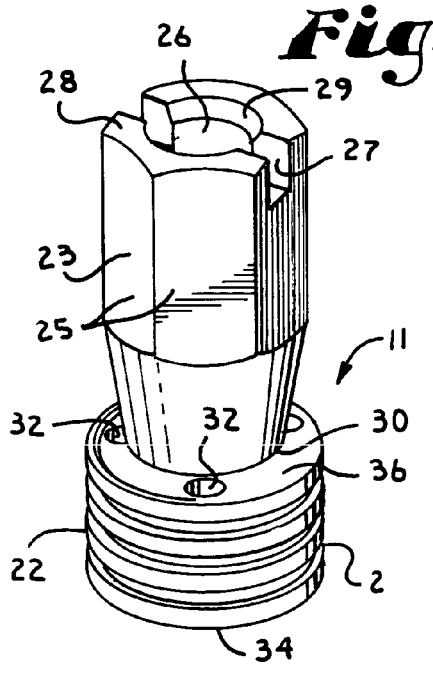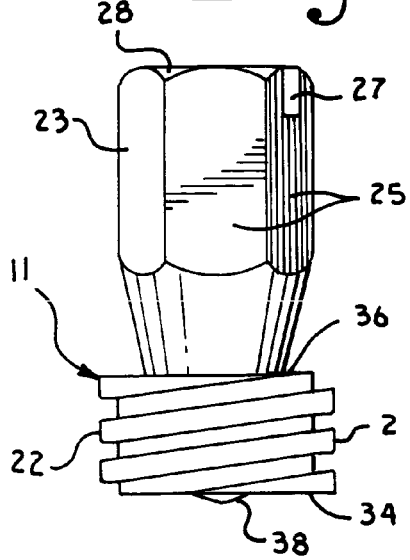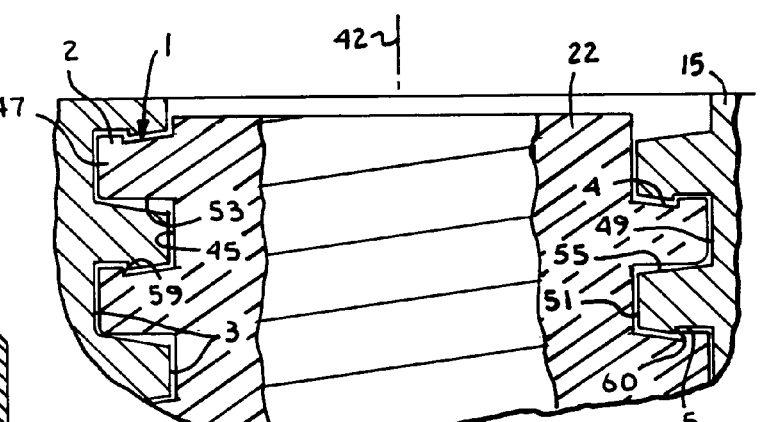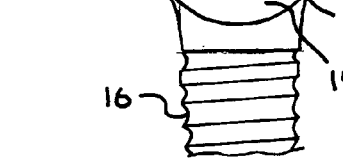

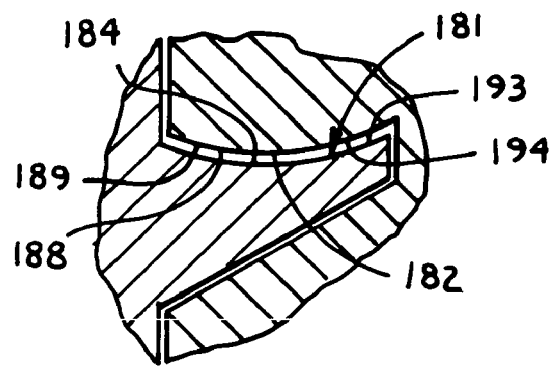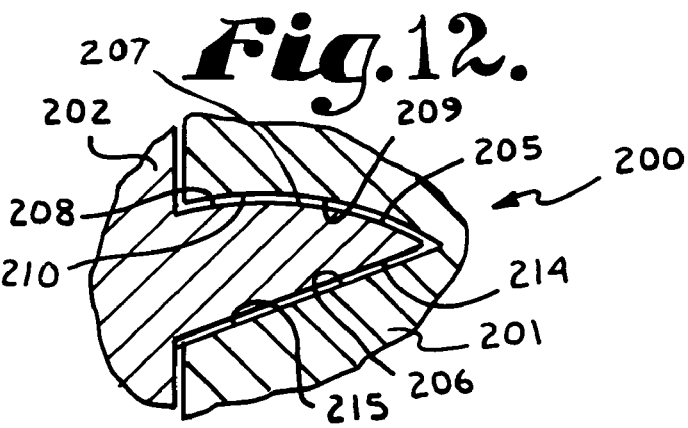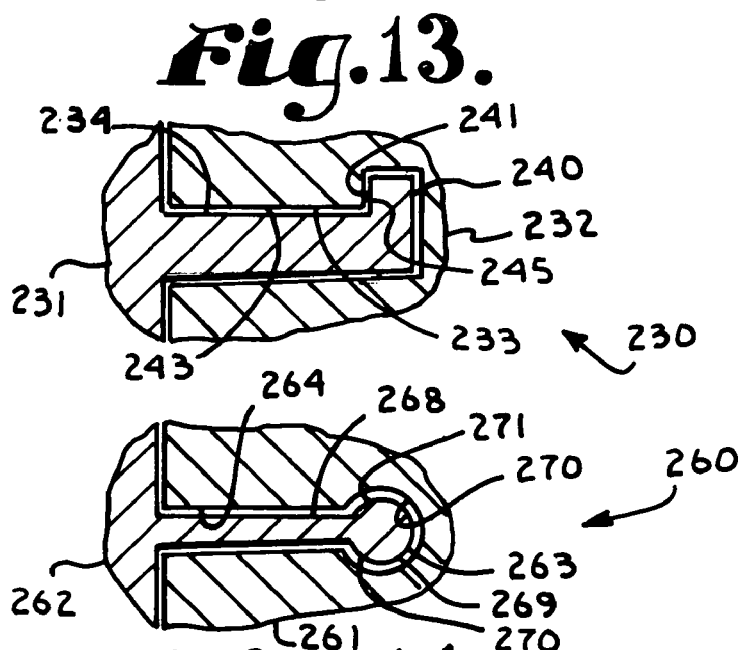

HELICAL WOUND MECHANICALLY INTERLOCKING MATING GUIDE AND ADVANCEMENT STRUCTURE

CROSS REFERENCE TO RELATED APPLICATION

The present application is a continuation of Ser. No. 10/236,123, filed Sep. 6, 2002, now U.S. Pat. No. 6,726,689.

BACKGROUND OF THE INVENTION

The present invention is directed to a structure for use in interlocking together two elements and, in particular, to a structure for joining together parts of a medical implant. The structure includes a first interlocking form on a closure and a mating second interlocking form on a receiver. The closure is operably rotated into the receiver. The first and second interlocking forms are both helically wound so that the first interlocking form advances relative to the second interlocking form, when the closure with the first interlocking form is inserted in the receiver and rotated. At least one of the first or second interlocking forms includes a projection that overlaps and radially locks with the other interlocking form when the two forms are mated.

Medical implants present a number of problems to both surgeons installing implants and to engineers designing them. It is always desirable to have an implant that is strong and unlikely to fail or break during usage. It is also desirable for the implant to be as small and lightweight as possible so that it is less intrusive on the patient. These are normally conflicting goals, and often difficult to resolve.

One particular type of implant presents special problems. In particular, spinal bone screws, hooks, etc. are used in many types of back surgery for repair of injury, disease or congenital defect. For example, spinal bone screws of this type are designed to have one end that inserts threadably into a vertebra and a head at an opposite end thereof. The head is designed to receive a rod or rod-like member in a channel in the head which rod is then both captured in the channel and locked in the head to prevent relative movement between the various elements subsequent to installation.

There are two different major types of bone screws and similar devices which are classified as closed headed and open headed. While the closed headed devices are highly effective at capturing and securing a rod, since the rod is threaded through an opening in the head, it is very difficult during surgery to thread the rod through the heads. This is because there are many heads and the rod is curved or the heads do not align. Consequently, the more screw heads that the rod must pass through, the more difficult it is to thread the rod into them.

The second type of head is an open head wherein a channel is formed in the head and the rod is simply laid in an open channel. The channel is then closed with a closure member. The open headed bone screws and related devices are much easier to use and in some situations must be used instead of the closed headed devices.

While the open headed devices are often necessary and often preferred for usage, there is a significant problem associated with them. In particular, the open headed devices conventionally have two upstanding arms that are on opposite sides of a channel that receives the rod member. The top of the channel is closed by a closure member after the rod member is placed in the channel. The closure can be of a slide in type, but such are not easy to use. Threaded nuts are sometimes used that go around the outside of the arms. Such nuts prevent splaying of the arms, but nuts substantially increase the size and profile of the implant which is not desirable. Many open headed implants are closed by plugs that screw into threads between the arms, because such have a low profile. However, threaded plugs have encountered problems also in that they produce radially outward forces that lead to splaying of the arms or at least do not prevent splaying that in turn loosens the implant. In particular, in order to lock the rod member in place, a significant force must be exerted on the relatively small plug or screw. The forces are required to provide enough torque to insure that the rod member is clamped or locked in place relative to the bone screw, so that the rod does not move axially or rotationally therein. This typically requires torques on the order of 100 inch-pounds.

Because open headed implants such as bone screws, hooks and the like are relatively small, the arms that extend upwardly at the head can be easily bent by radially outward directed forces due to the application of substantial forces required to lock the rod member. Historically, early closures were simple plugs that were threaded with V-shaped threads and which screwed into mating threads on the inside of each of the arms. But, as noted above, conventionally V-shaped threaded plugs tend to splay or push the arms radially outward upon the application of a significant amount of torque, which ends up bending the arms sufficiently to allow the threads to loosen or disengage and the closure to fail. To counter this, various engineering techniques were applied to allow the head to resist the spreading force. For example, the arms were significantly strengthened by increasing the width of the arms by many times. This had the unfortunate effect of substantially increasing the weight and the profile of the implant, which was undesirable.

Many prior art devices have also attempted to provide outside rings or some other type of structure that goes about the outside of the arms to better hold the arms in place while the center plug is installed and thereafter. This additional structure may cause the locking strength of the plug against the rod to be reduced which is undesirable, especially when the additional structure is partly located beneath the plug. Also, the additional elements are unfavorable from a point of view of implants, since it is typically desirable to maintain the number of parts associated with the implants at a minimum and, as noted above, the profile as minimal as possible.

Other designers have attempted to resolve the splaying problem by providing a closure with a pair of opposed radially extending wedges or flanges that have mating structure in the arms of the implant. Such devices serve as a closure and do somewhat resist splaying of the arms, but are often very difficult to use. In particular, the rods normally have some curvature as the rods are bent to follow the curvature of the spine and normally bow relative to the bottom of the bone screw channel that receives such a rod. The rod thus fills much of the channel and must be "unbent" to rest on the bottom of the channel and be held securely in place. Therefore, the rod is preferably compressed by the plug and unbent by advancement of the plug into the channel in order to assume that the plug will securely hold the rod and that the rod and plug will not loosen when post assembly forces are placed on the rod. Because it takes substantial force to unbend the rod, it is difficult to both place the plug fully in the channel and rotate it for locking while also trying to line up the wedges with the mating structure. It is much easier to align the plug mating structure with the mating structure of the arms at the top of the arms and then rotate the plug so as to screw the plug into a plug receiver to advance the plug toward the rod. In this way the plug starts applying significant force against the rod only after parts of the mating structure have at least partly joined at which time torque can be applied without having to worry about alignment. It is noted that where wedges are used, the cross section of the structure changes therealong so that the device "locks up" and cannot turn further after only a small amount of turning, normally ninety degrees.

Consequently, a lightweight and low profile closure plug was desired that resists splaying or spreading of the arms while not requiring significant increases in the size of the screw or plug heads and not requiring additional elements that encircle the arms to hold the arms in place.

It is noted that the tendency of the open headed bone screw to splay is a result of the geometry or contour of the threads typically employed in such devices. In the past, most bone screw head receptacles and screw plugs have employed V-shaped threads. V-threads have leading and trailing sides oriented at angles to the screw axis. Thus, torque on the plug is translated to the bone screw head at least partially in an axial direction, tending to push or splay the arms of the bone screw head outward in a radial direction. This in turn spreads the internally threaded receptacle away from the thread axis so as to loosen the plug in the receptacle.

The radial expansion problem of V-threads has been recognized in various types of threaded joints. To overcome this problem, so-called "buttress" threadforms were developed. In a buttress thread, the trailing or thrust surface is oriented perpendicular to the thread axis, while the leading or clearance surface remains angled. This theoretically results in a neutral radial reaction of a threaded receptacle to torque on the threaded member received.

Development of threadforms proceeded from buttress threadforms which in theory have a neutral radial effect on the screw receptacle to reverse angled threadforms which theoretically positively draw the threads of the receptacle radially inward toward the thread axis when the plug is torqued. In a reverse angle threadform, the trailing side of the external thread is angled toward the thread axis instead of away from the thread axis, as in conventional V-threads. While buttress and reverse threadforms reduce the tendency to splay, the arms can still be bent outward by forces acting on the implant and the threads can be bent by forces exerted during installation. Therefore, while certain threadforms may not exert radial forces during installation, at most such threadforms provide an interference or frictional fit and do not positively lock the arms in place relative to the closure plug.

Finally, it is noted that plugs of this type that use threadforms are often cross threaded. That is, as the surgeon tries to start the threaded plug into the threaded receiver, the thread on the plug is inadvertently started in the wrong turn or pass of the thread on the receiver. This problem especially occurs because the parts are very small and hard to handle. When cross threading occurs, the plug will often screw part way in the receiver and then "lock up" so that the surgeon is led to believe that the plug is properly set. However, the rod is not tight and the implant fails to function properly. Therefore, it is also desirable to have a closure that resists crossthreading in the receiver.

SUMMARY OF THE INVENTION

A non threaded guide and advancement structure is provided for securing a set screw, plug or closure in a receiver: Preferably the receiver is a rod receiving channel in an open headed bone screw, hook or other medical implant wherein the channel has an open top and is located between two spaced arms of the implant.

The guide and advancement structure has a first part or interlocking form located on the closure and a second part or interlocking form that is located on the interior of the receiving channel.

Both parts of the guide and advancement structure are spirally or more preferably helically wound and extend about the closure and receiving channel for at least one complete 360° pass or turn. Preferably, both parts include multiple turns such as 2 to 4 complete 360° rotations about the helixes formed by the parts. The helixes formed by the parts are coaxial with the closure when the closure is fully received in or being rotated into the receiving channel between the arms.

One major distinguishing feature of the guide and advancement structure is that each of the parts include elements that mechanically interlock with the opposite part as the closure is rotated and thereby advanced into the receiving channel toward the bottom of the channel and into engagement with a rod received in the channel.

Each part of the guide and advancement structure preferably has a generally constant and uniform cross section, when viewed in any cross sectional plane fully passing through the axis of rotation of the closure during insertion, with such uniform cross section extending along substantially the entire length of the interlocking form. It is noted that at opposite ends of each interlocking form, the form must be feathered or the like and so the cross section does change some at such locations, while retaining part of the overall shape. In particular, the outer surfaces of each interlocking form remain sufficiently uniform to allow interlocking forms to be rotated together and slide tangentially with respect to each other through one or more complete turns of the closure relative to the receiving channel. Each part may be continuous from near a bottom of the closure or receiving channel to the top thereof respectively. In certain circumstances one or both parts may be partly discontinuous, while retaining an overall helical configuration with a generally uniform cross sectional shape. When the interlocking form has multiple sections due to being discontinuous, each of the sections has a substantially uniform cross section along substantially the entire length thereof.

In order to provide an interlocking structure, the parts of the structure include helical wound projections or interlocking forms that extend radially outward from the closure and radially inward from the receiving channel. The interlocking forms may be of many different shapes when viewed in cross-section with respect to a plane passing through the axis of rotation of the plug during insertion. In general, the interlocking forms increase in axial aligned width or have a depression at a location spaced radially outward from where the interlocking form attaches to a respective closure or receiving channel, either upward (that is, parallel to the axis of rotation of the closure in the direction from which the closure comes or initially starts) or downward or in both directions. This produces a first mating element that is in the form of a protrusion, bump, ridge, elevation or depression on the interlocking form that has a gripping or overlapping portion. The opposite interlocking form has a second mating element with a gripping or overlapping portion that generally surrounds or passes around at least part of the first mating element in such a way that the two are radially mechanically locked together when the closure is advanced into the receiving channel.

Therefore, in accordance with the invention a mating and advancement structure is provided for joining two devices, that are preferably medical implants and especially are an open headed implant that includes a rod receiving channel and a closure for closing the receiving channel after the rod is received therein. The mating and advancement structure includes a pair of mateable and helical wound interlocking forms with a first interlocking form located on an outer surface of the closure and a second interlocking form located on an inner surface of the receiving channel or receiver. The first and second interlocking forms are startable so as to mate and thereafter rotatable relative to each other about a common axis so as to provide for advancement of the closure into the receiver during assembly when the closure interlocking form is rotated into the receiver interlocking form. The first and second interlocking forms have a helical wound projection that extends radially from the closure and the receiver respectively. Each interlocking form projection has a base that is attached to the closure or receiver respectively and preferably includes multiple turns that may each be continuous or partially discontinuous with constant or uniform cross-sectional shape. The interlocking forms have substantial axial width near an outer end thereof that prevents or resists misalignment of the interlocking form during initial engagement and rotation thereof.

After assembly, in some embodiments each turn of each projection generally snugly engages turns of the other projection on either side thereof. In other embodiments there must be sufficient tolerances for the parts to slide tangentially, so that when thrust surfaces of the interlocking forms are very close during tightening, some gap occurs on the leading side of the closure interlocking form. In such a case the portions of the interlocking forms on the thrust side thereof lock together and prevent radial splaying. Located radially spaced from where the base of each projection is attached to either the closure or receiver respectively, is an axially extending (that is extending in the direction of the axis of rotation of the plug or vertically) extension or depression. The opposite or mating interlocking form has elements that wrap around or into such extensions or depressions of the other interlocking form. That is, the forms axially interdigitate with each other and block radial movement or expansion. In this way and in combination with the interlocking forms preferably being snug relative to each other with sufficient clearance to allow rotation, the interlocking forms, once assembled or mated lock to prevent radially slipping or sliding relative to each other, even if the base of one or both is bent relative to the device upon which it is mounted. It is possible that the cross section of the projection (in a plane that passes through the plug axis of rotation of the plug) of each section of each turn or pass of the interlocking form be the same, although this is not required in all embodiments. For example, part of the interlocking form may be missing in the region between opposed arms when assembly is complete as this area is not required to hold the arms together.

Preferably the present invention provides such an interlocking form for use in a medical implant closure which resists splaying tendencies of arms of a receiver. In one embodiment the interlocking form of the present invention provides a compound or "non-linear" surface on a trailing face, thrust face or flank of the interlocking form.

The interlocking form located on the closure in one embodiment is helically wound about a cylindrical outer surface of the closure and has an inner radius or root, and an outer radius or crest that remain constant over substantially the entire length of the interlocking form. The receiver has a mating or similar shaped interlocking form wound about the interior thereof. In this embodiment the interlocking form has leading or clearance surfaces and trailing or thrust surfaces, referenced to the direction of axial movement of the form when rotated into one another.

The structure also includes an internal helical wound interlocking form located on an internal surface of a receiver member and having an outer root and an inner crest. The internal interlocking form has thrust surfaces which are oriented in such a direction so as to be engaged by the thrust surfaces of the external interlocking form of a member engaged therewith.

In the interlocking forms of this series of embodiments, the thrust surfaces are "non-linear" or compound. That is, the thrust surfaces have a non-linear appearance when represented in cross section. The purpose for the non-linear or compound surface is to provide a portion of the thrust surface which is oriented in such a direction as to resist a tendency of the receiver to expand when tightening torque is applied to rotate the interlocking forms into a mating relationship. As applied to a closure for an open headed bone implant screw, the non-linear or compound surfaces of the interlocking forms resist splaying tendencies of the arms of the head. The objective of the interlocking form is not necessarily to generate a radially inwardly directed force on the receptacle in tightening the fastener (although this may occur in some embodiments), but importantly to resist and prevent outward forces generated by engagement of the closure with the closure receptacle or by other forces applied to the components joined by the closure and closure receptacle. It is noted that the present invention requires that only a portion of the thrust surfaces of a closure be so configured as to face toward the closure axis and only a portion of thrust surfaces of a closure receptacle face away from the axis.

While the axial extension or depression in one series is located on the thrust or trailing surface, it is also possible for such to be located on the opposite or leading surface or both.

In this series of embodiments, a section of the interlocking form at the crest, that is located radially outward of the root, is enlarged in cross sectional area to create a gripping, locking or stopping surface that resists slippage or sliding in a radial direction relative to an opposed interlocking form. In a complementary manner, a section of the interlocking form between the root and the crest and that is radially spaced from the root is enlarged in cross sectional area to create a gripping, locking or stopping surface that engages a like surface of the opposite interlocking form. The enlarged sections of the inner and outer interlocking forms are created, in practice, by cutting, molding, machining or the like grooves or channels or the like into a radially inward portion of the thrust surface of the external interlocking form and mating grooves or channels into a radially outward portion of the thrust surface of the internal interlocking form. Such grooves or channels may be formed by specially shaped taps and dies, cutting elements or by other suitable manufacturing processes and technologies, including molding.

The interlocking forms of the present invention may be implemented in a variety of configurations of non-linear, compound, or complex trailing and/or leading surfaces. The nomenclature used to describe variations in the interlocking forms of the present invention is especially referenced to the external interlocking forms located on a closure, with complementary or similar shapes applied to the internal interlocking forms on a receiver. In an axial shoulder interlocking form of the present invention, a somewhat squared gripping shoulder is formed on an outer periphery of the external interlocking forms and an inner gripping surface on the internal interlocking forms. The axial shoulder interlocking form results in complementary cylindrical surfaces on the external and internal interlocking forms which mutually engage when the fastener or closure is rotated into a closure receptacle.

In an axial extending bead interlocking form, the external interlocking form is provided with a rounded peripheral bead or lateral lip which projects in an axial direction along the interlocking form crest and a complementary rounded concave channel in the internal interlocking form. The reverse occurs with the internal interlocking form.

In a radial bead interlocking form, a rounded bead enlargement is formed on the radially outward periphery at the crest of the external interlocking form, while the internal interlocking form is formed in a complementary manner to receive the radial bead interlocking form.

A scalloped or scooped interlocking form is, in effect, a reciprocal of the axial bead interlocking form and has a rounded channel or groove located along the thrust surface of the external interlocking form, with a complementary rounded convex bead shape formed associated with the internal interlocking form.

A variation of the axial bead interlocking form is a medial bead embodiment. In the medial bead interlocking form, a bead projects from a base thrust surface of an external interlocking form in an axial direction at a location medially between the root and crest of the interlocking form. In a complementary medial bead internal interlocking form, an axial groove is formed in a base thrust surface between the root and crest. In a medial groove interlocking form, an axial groove is formed in a base thrust surface of the external interlocking form medially between the root and crest, while the internal interlocking form has an axial bead located medially between the root and crest.

Variations in the above described interlocking forms are envisioned with respect to relative extensions or enlargements and depressions or depth of grooves of the various interlocking forms. In some variations, the opposite interlocking forms have the same but reversed and inverted cross section, whereas in others the cross section of the paired interlocking forms is different. It is noted that many other configurations of interlocking forms with non-linear, compound or complex thrust surfaces are envisioned, which would be encompassed by the present invention.

The interlocking forms of the present invention find particularly advantageous application in various types of bone implant devices, although the inventive interlocking forms are not limited to such use. The interlocking forms also have advantages in reducing misalignment problems of cross-interlocking and misinterlocking of interlocking forms when the opposed interlocking forms are joined and rotated which is commonly encountered in such devices when threads of various types are used.

OBJECTS AND ADVANTAGES OF THE INVENTION

Therefore, objects of the present invention include: providing an improved closure for an open headed lightweight and low profile medical implant wherein the implant has a pair of spaced arms and the closure closes between the arms; providing such a closure which includes a pair of opposed interlocking forms and which resists tendencies of the arms to splay or separate during insertion of the closure, to thereby reduce the likelihood of failure of the implant and closure system during use; providing such a closure which can be installed at comparatively high torques to thereby secure the closure in the receiver channel and in certain embodiments to also lock a rod member in the open head of the implant where the closure engages and is urged against the rod by rotation in a receiver channel of the remainder of the implant; providing an interlocking form for such a closure which resists tendencies of parts of the channel receiver to expand radially outward in response to high torque applied to the closure; providing such an interlocking form in which the respective thrust surfaces of mating internal and external interlocking forms are "non-linear", compound, or complex to provide only a portion of each trailing or leading surface which is oriented in such a direction as to resist the splaying or expanding tendencies of parts of the receiving channel; providing such an interlocking form wherein the interlocking form has a base that is secured to a member and the interlocking form extends radially outward from the base with an axial extension starting at or radially spaced from the base and further wherein the interlocking form has an extension or depression that extends in an axial direction relative to an axis of rotation of the interlocking form and which mates with the opposite interlocking form so as to grip or hold such extension or depression and yet further wherein opposed interlocking forms are rotatable relative to each other during assembly, but are preferably sufficiently snug or located sufficiently near to one another to prevent one interlocking member to slide radially past another when torque is applied thereto or when forces act on the implant; providing embodiments of such an interlocking form having an enlarged radial cross section wherein the enlargement is spaced radially outward of a root of the external interlocking form and a complementary enlarged cross section spaced radially inward of a root of the internal interlocking form; providing embodiments of such an interlocking form having a first groove or channel formed in a surface inward of a periphery of an external interlocking form and a complementary second groove or channel formed in a surface inward of a periphery of an internal interlocking form so that the paired interlocking forms overlap and radially lock together upon assembly; providing embodiments of such an interlocking form in which the enlarged peripheries and grooves of the external and internal interlocking form have or form angularly defined or axially extending shoulders; providing embodiments of such an interlocking form in which the enlarged peripheries of the external and internal interlocking form have or form arcuately defined or rounded shoulders; providing such interlocking forms having a generally uniform cross section along a substantial length thereof; providing such interlocking forms that rotate relative to each other at least one full turn upon assembly; providing such interlocking forms which reduce the likelihood of cross-interlocking or misinterlocking problems of members during initial joining; providing such interlocking forms which can be formed relatively economically using appropriate metal forming technologies; and providing interlocking forms, particularly for implant and bone fixation hardware, which are economical to manufacture, which are secure and efficient in use, and which are particularly well adapted for their intended usage.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a closure for an open headed bone screw that has a helical wound gripping interlocking form in accordance with the present invention mounted thereon.

FIG. 2 is a side elevational view of the closure.

FIG. 3 is a side elevational view at a reduced scale and illustrates an interlocking form of the closure mated with and installed in a companion interlocking form on an open headed bone screw to capture a fixation rod within a head of the bone screw and with the head of the bone screw partially broken away to illustrate detail thereof.

FIG. 4 is an enlarged fragmentary side elevational view of the bone screw head with the closure installed therein, the closure and bone screw head incorporating the interlocking form according to the present invention with portions broken away to show detail thereof.

FIG. 11 is a fragmentary cross sectional view of a seventh modified bone screw and closure, similar to the embodiment in FIG. 10, showing a pair of interlocking forms in accordance with the present invention.

FIG. 12 is a fragmentary cross sectional view of an eighth modified embodiment of a bone screw and closure showing a pair of interlocking forms in accordance with the invention.

FIG. 13 is a fragmentary cross sectional view of an ninth modified embodiment of a bone screw and closure showing a pair of interlocking forms in accordance with the invention.

FIG. 14 is a fragmentary cross sectional view of an tenth modified embodiment of a bone screw and closure showing a pair of interlocking forms in accordance with the invention.

DETAILED DESCRIPTION OF THE INVENTION

Figure 5:
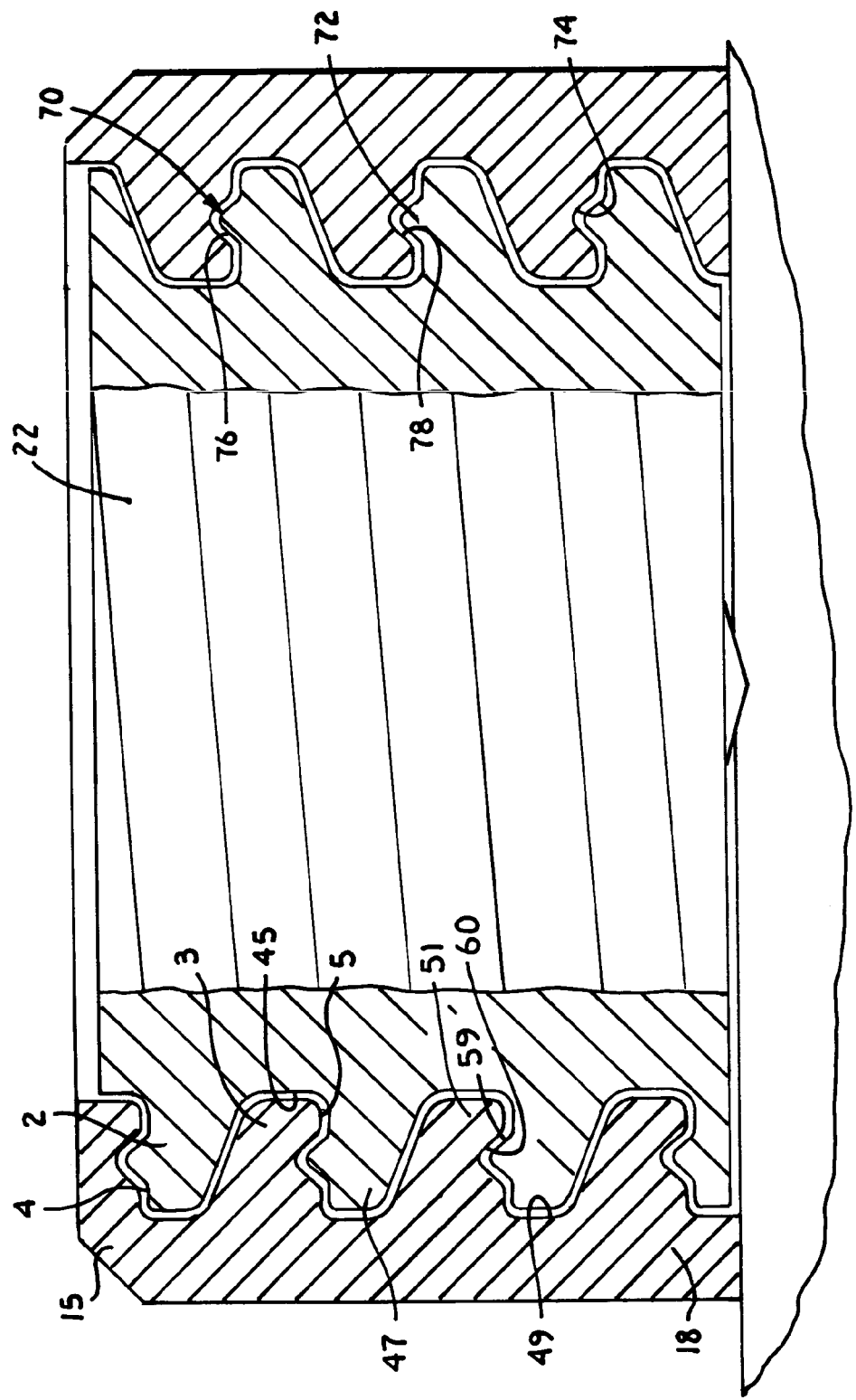
FIG. 5 is a view similar to FIG. 4 and illustrates details of first modified bone screw and closure showing a medial bead embodiment of an interlocking form of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a gripping interlocking form arrangement incorporating a non-linear or compound surface which embodies the present invention. The interlocking form arrangement 1 includes an external interlocking form 2 and internal interlocking form 3 which have respective thrust surfaces or load flanks 4 and 5 (FIG. 4) and which are used as pairs. The interlocking form arrangement 1 may be used on any of a number of interlocking formed devices, such as an implanted bone fixation system 8 (FIG. 3), including a receiver or open headed implant member 10 which receives a closure or closure member 11 (FIGS. 1 and 2) to secure a fixation member 12 therein. In the interlocking form arrangement 1 of the present embodiment, the thrust surfaces 4 and 5 are non-linear or compound in such a manner as to resist tendencies of the receptacle 10 to splay or expand when the closure member 11 is rotated therein.

The illustrated implant member 10 is also referred to as an open headed bone screw and includes a U-shaped implant head 15 and a threaded shank 16. The head 15 has a pair of spaced apart arms 18 forming a rod receiving channel 19. The arms 18 are radially inwardly tapped with the internal interlocking form 3 that is discontinuous between sides to receive the closure member 11. The illustrated shank 16 tapers to a point (not shown) and is externally threaded and adapted to be received in a bone, such as a vertebra, to anchor the rod 12 to such a bone.

The illustrated closure member 11 includes a plug, base section or base 22 and a break off head section 23 that breaks from the base 22 at a preselected torque. It is foreseen that such a closure could be made without a breakoff head and other structure could be added for torquing or removing the base section. Furthermore, it is foreseen that such a base both captures the rod and locks the rod as in the embodiment illustrated in FIGS. 1 to 4 or, alternatively, that the base could just capture the rod and a set screw could be used in a threaded bore in the base to lock the rod in place. The base section 22 is provided with the external interlocking form 2 which is compatible with the internal interlocking form 3 of the bone screw head 15. Both interlocking forms 2 and 3 are helically wound and rotatably mateable together through rotation or turning of the closure member 11 about a central axis 42 thereof. The head 23 includes structure for positive engagement by an installation tool (not shown) to install the closure member 11 in the bone screw member 10. The structure that allows for installation of the illustrated break off head 23 includes faces 25 forming a hexagonal shape or "hex" head to receive a complementary hexagonally shaped installation driver or tool. The head 23 also includes a central bore 26 and a cross bore slot 27. The outer end of the head 23 is chamfered at 28, and the bore 26 is provided with an interior conical countersink at 29. The region where the head 23 meets the base 22 is reduced in cross sectional thickness to form a weakened breakaway or fracture region 30. The breakaway region 30 is designed so that the head 23 separates from the base 22 when a selected torque is applied by the installation tool, as is diagrammatically illustrated by breaking away of the head 23 in FIG. 3. The base 22 is preferably provided with structure to facilitate removal of the base 22 from the implant head 15, such as the illustrated removal bores 32. The bores 32 may be formed by drilling from a lower end surface 34 of the plug 22, since an upper end surface 36 of the plug 22 is normally not accessible for drilling the bores 32 prior to break-off of the head 23. It is foreseen that many different types of removal devices or structures can be utilized with the base such as: axially aligned bores with hex, torx or other multifaceted cross-section, step down bores for engagement by an easy out, bores at the periphery or non axially aligned on the face of the base, bores with a left handed thread or the like. Further, the same structure used to torque the base on installation may be used to remove the base.

The base 22 is rotated into the receiving member of the bone screw head 15 to clamp the fixation rod 12 therein for any of a variety of surgical purposes. In general, the rod 12 is used to fix the position of a bone or portion of a bone, such as a plurality of vertebrae. The rod 12 may be anchored relative to some vertebrae and, in turn, used to secure other vertebrae in desired positions or orientations or used to properly align a series of vertebrae. It is generally required that the union formed between the bone screw 10, closure 11 and the rod 12 be very tight or snug to avoid relative movement therebetween. The fixation system 8 preferably employs structure that positively engages and seats the head 15 and/or the base 22 with respect to the rod 12, such as a conical set point 38 formed on the bottom surface 34 of the base 22 which engages the rod 12. The point 38 positively "bites" into the surface of the rod 12 to help prevent rotational or axial movement of the rod 12 relative to the screw 10. Alternatively or in combination with a point 38, other structures may be used to positively engage the closure plug 22 with the rod 12, such as a sharp edged coaxial ring (not shown) having a V-shaped cross section formed on the lower surface 34 of the base 22 or point extending upwardly from the channel.

The interlocking forms 2 and 3 are helical and are intended to advance the closure member 11 linearly along the axis of rotation 42 of the closure member 11 and the interlocking forms 2 and 3 relative to another member as the closure member 11 is rotated relative to the bone screw 10. A spatial reference for such rotation and linear movement is along the axis 42 (FIG. 4). The axis 42 locates the coincident axes of the external or radially outward interlocking form 2 of the base 22 and the internal or radially inward interlocking form 3 of the head 15, when the base 22 is inserted into the head 15 by starting at the top of the interlocking form 3 (top is up in FIG. 4) and rotated. The base 22 has a basic cylindrical shape, and the external interlocking form 2 includes a root 45 and a crest 47 formed by cutting a helical wound channel of the desired cross section into the original surface of the base 22. The crest 47 of the external interlocking form 2 has a greater radius than the root 45. In a like manner, the internal interlocking form 3 of the head 15 of the screw 10 has a helical channel under cut thereinto, forming a root 49 and crest 51. The root 49 of the internal interlocking form 3 has a greater radius than the crest 51.

The thrust surfaces 4 and 5 respectively of the external and internal interlocking forms 2 and 3 engage frictionally when the base 22 is rotated into the head 15. The thrust surfaces 4 and 5 are located on the trailing sides respectively of the crests 47 and 51, as referenced to the tightening direction movement of the base 22 into the head 15. In general, there is minimal contact between clearance surfaces or stab flanks 53 and 55 when the base 22 is rotated in a tightening direction into the screw head 15 to allow rotation. The clearance surfaces 53 and 55 may frictionally engage when the base 22 is rotated in a reverse direction to remove it from the screw head 15.

Frictional engagement of the thrust surfaces 4 and 5 due to rotation causes the base 22 to be advanced linearly along the axis 42 into the screw head 15. However, once the base 22 "bottoms out" by contact of the lower surface 34 or the set point 38 with the rod 12 and the rod 12 is unbent and pushed downwardly as far as it will go into the channel or seat 19, further rotation of the base 22 cannot result in further linear movement of the base 22 within the head 15. The interlocking forms 2 and 3 thereafter are radially locked together and each turn or pass of the forms 2 and 3 is preferably sufficiently snug with respect to turns of the opposite interlocking form to prevent either form 2 or 3 from slipping or sliding radially past one another upon application of additional torque or with application of forces due to usage by the patient.

The various compound, complex, or non-linear interlocking form arrangements of the present invention are intended to resist splaying tendencies of the arms 18. In particular, each thrust surface 4 and 5 of the interlocking forms 2 and 3 have a gripping, blocking or splay resisting surface 59 or 60 respectively which is oriented in such a direction as to resist splaying of the arms 18 of the screw head 15 when the base 22 is rotated to a high degree of torque. On the external interlocking form 2, the splay resisting surface 59 is directed generally toward or faces the axis 42. Conversely, on the internal interlocking form 3, the splay resisting surface 60 is directed generally away from or faces away from the axis 42. Each of the surfaces 59 and 60 in this manner wrap over or around the opposite and block substantial radially relative movement there between. It is especially noted that the surfaces 59 and 60 are extensions of the interlocking forms 2 and 3 in an axial direction (that is parallel to the axis 42 or up and down as seen in FIG. 4). This axial extension is spaced away from the juncture of the interlocking forms 2 and 3 with the base 22 and screw 10. It is foreseen that such an extension can take many shapes and configurations (some of which are shown herein) and may also functionally be depressions or grooves. In each case the paired interlocking forms, such as forms 2 and 3, overlap each other and are snug about each other so as to prevent substantial relative radial slippage or movement between them during and after assembly of the base 22 into the bone screw 10.

FIG. 5 illustrate a non-linear or compound thrust surface interlocking form arrangement 70 which is of a medial bead interlocking form type. The interlocking form arrangement 70 a thrust surface 4 located on a plug 22 and internal interlocking form 3 with thrust surfaces 5 within a head 15 of a bone screw 10. The thrust surfaces 4 and 5 are contoured to provide complementary, interacting, splay resisting surfaces 59 and 60 on the external and internal interlocking forms 2 and 3 respectively. The external interlocking form 2 is provided with a bead 72 on the thrust surface 4, and the internal interlocking form 3 is provided with a complementary channel or groove 74 formed into the thrust surface 5. The illustrated thrust surfaces 4 and 5 are substantially perpendicular to the axis 42; however, such surfaces may alternatively be angled somewhat with respect to the axis 42 so as to slope downward or upward as the surface extends radially outward.

The bead 72 is located at a radius which is between or medial with respect to the root 45 and crest 47 of the external interlocking form 2. Similarly, the groove 74 is located at a radius which is medial to the root 49 and crest 51 of the internal interlocking form 3. The illustrated bead 72 and groove 74 are rounded and somewhat triangular in cross section. Alternatively, the bead and groove 72 and 74 could be pointed and triangular, squared off, or semicircular. It should also be noted that the bead and groove 72 and 74 could be replaced by a medial groove formed in the external interlocking form 2 on the thrust surface 4 and a medial bead formed on the thrust surface 5 of the internal interlocking form 3. An inwardly facing surface 76 of the bead 72 forms the splay resisting surface 59 thereof, while an outwardly facing surface 78 of the groove 74 forms the splay resisting surface of the groove 74. Engagement of the splay resisting surfaces 76 and 78, respectively of the bead 72 and groove 74, resists tendencies of the arms 18 of the screw head 15 to splay when the closure base 22 is rotated into the head 15.

FIGS. 6 to 14 illustrate further variations in the paired interlocking forms of the present invention. In each case the base closure and bone screw, except as noted with respect to the interlocking forms, of the variations shown in FIGS. 6 to 14 are essentially the same as those shown in FIGS. 1 to 4, so only differing detail of the interlocking form structure will be described in detail and reference is made to the description given for FIGS. 1 to 4 for the remaining detail.

Figure 6:
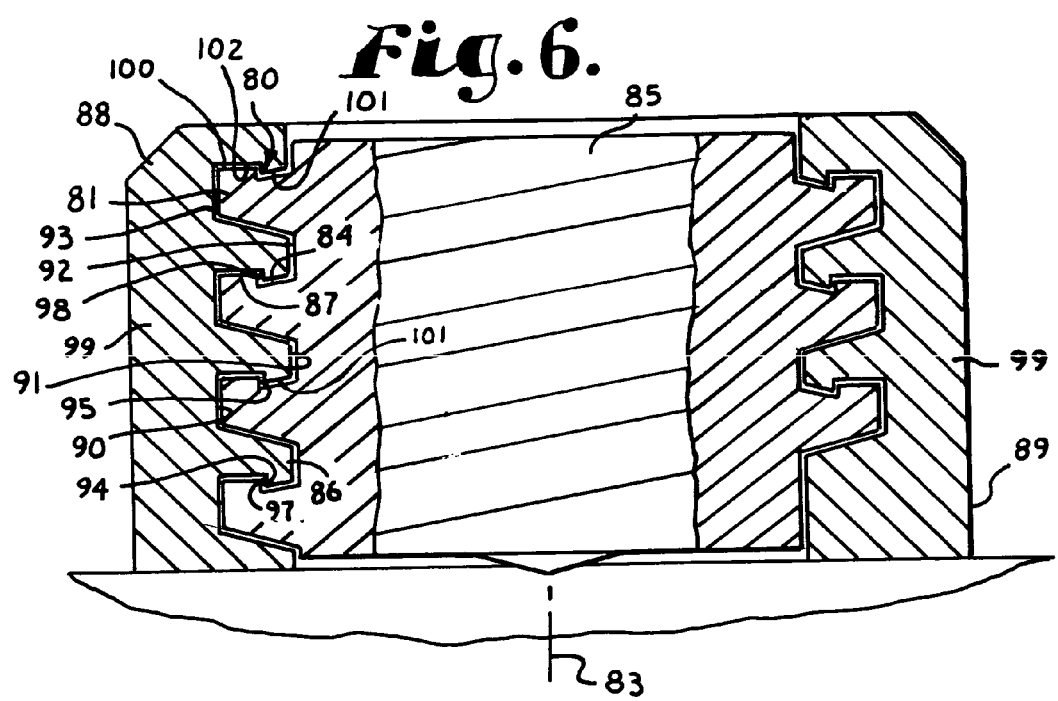
FIG. 6 is view similar to FIG. 4 and illustrates details of a second modified bone screw and closure showing an axial aligned shoulder embodiment of an interlocking form of the present invention.

In FIG. 6, a guide and advancement structure 80 includes the external interlocking form 81 having an axially aligned shoulder or flange-like shaped configuration when view in cross section in a plane passing through an axis of rotation 83. The interlocking form 81 has a thrust surface 84 on a base 85. The structure 80 also has an internal interlocking form 86 with a thrust surface 87 within the head 88 of a bone screw 89. The internal interlocking form 86 has a root 90 and a crest 91, while the external interlocking form 81 includes a root 92 and crest 93. The thrust surface 84 of the external interlocking form 81 includes an axially oriented or cylindrical shoulder 94 which forms a splay resisting surface 95 thereof.

Similarly, the thrust surface 87 of the internal interlocking form 86 includes a mating or complementary axially oriented or cylindrical shoulder 97 which forms a splay resisting surface 98. Engagement of the splay resisting surfaces 95 and 98 resists tendencies of the arms 99 of the head 88 to splay when the plug or base 85 is rotated into the head 88 and torqued tightly or at later times during usage. It is foreseen that a variation of the axial shoulder interlocking form would provide shoulders at inclined angles (not shown) to the axis 42. The illustrated splay resisting shoulder 94 is formed by a rectangular cross section bead 100 formed on the thrust surface 84 of the external interlocking form 81. Similarly, splay resisting shoulder 97 is formed by a somewhat rectangularly cross section shaped bead or foot portion 101 adjacent a groove 102 for receiving bead 100 and formed in the thrust surface 87 of the internal interlocking form 86. The interlocking forms 81 and 86 have a general flange-like shape configuration when viewed in cross section that is also some what L-shaped with the beads 100 and 101 forming feet of the flange shape that overlap and lock so as to prevent substantial radial movement of the arms 99 of the bone screw 89 relative to the closure plug base 85.

Figure 7:
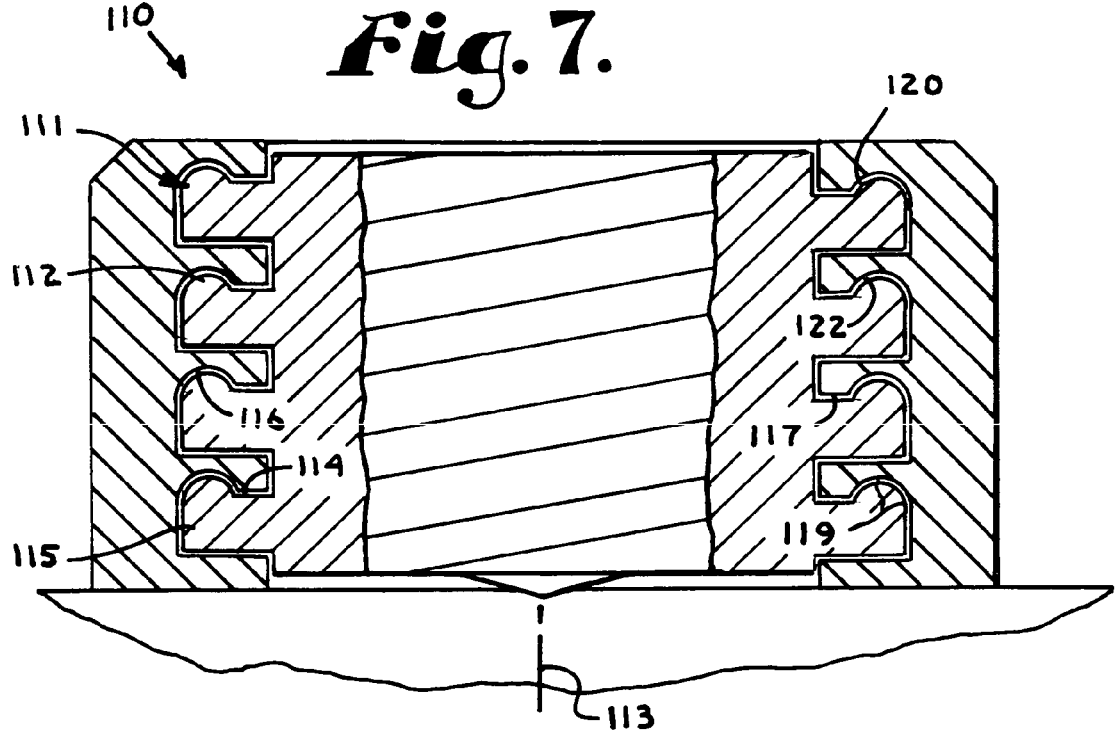
FIG. 7 is a view similar to FIG. 4 and illustrates details of a third modified bone screw and closure showing an axial bead embodiment of an interlocking form of the present invention.
Figure 8:
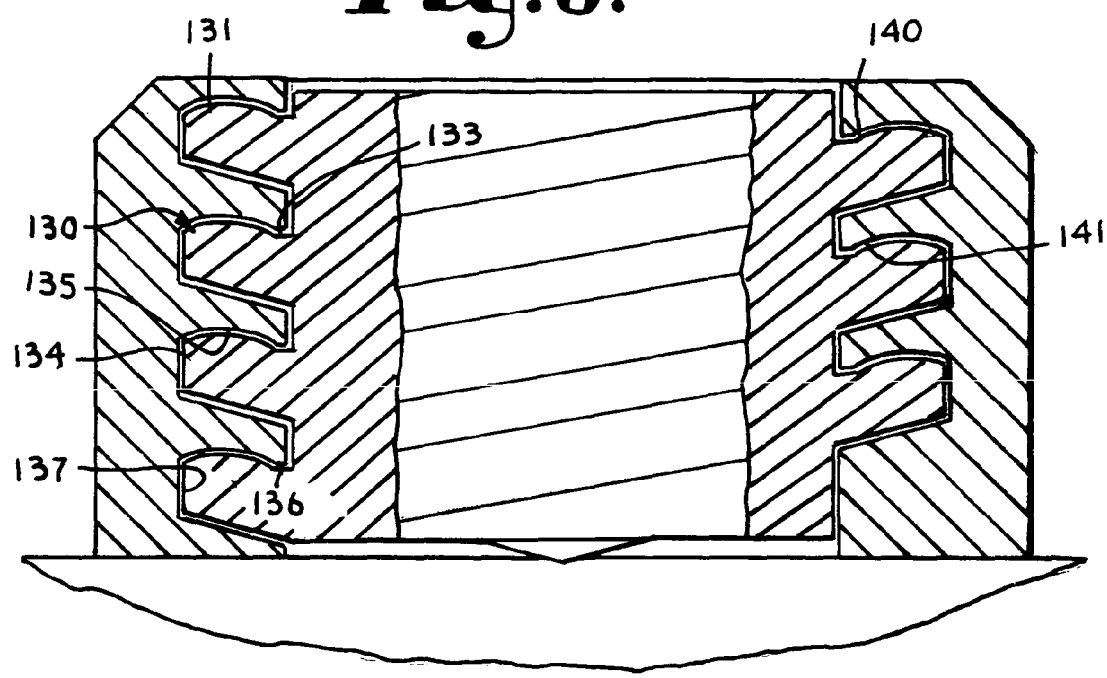
FIG. 8 is a view similar to FIG. 4 and illustrates details of a fourth modified bone screw and closure showing a shallow axial bead embodiment of an interlocking form of the present invention.

FIGS. 7 and 8 illustrate further variations of the axial shoulder interlocking structure 110 and 130 respectively in the form of a rounded axial bead interlocking form 111 shown in FIG. 7 and a shallow rounded axial bead interlocking form 131 in FIG. 8. The rounded axial bead interlocking form 111 includes a rounded bead 112 projecting in a direction parallel to an axis 113. The bead 112 is formed on a thrust surface 114 of an external interlocking form 115 and a rounded groove 116 is formed on a thrust surface 117 of an internal interlocking form 119. The bead 112 includes a splay resisting surface 120, while the groove 116 also includes a splay resisting surface 122.

In a similar manner, the shallow rounded axial bead interlocking form 130 includes a shallow rounded bead 131 formed on a thrust surface 133 of an external interlocking form 134 and a shallow rounded groove 135 formed on a thrust surface 136 of an internal interlocking form 137. The bead 131 includes a splay resisting surface 140, and the groove 135 includes a splay resisting surface 141. The surfaces 140 and 141 engage and abut to resist splaying or significant radial separation movement therebetween.

Figure 9:
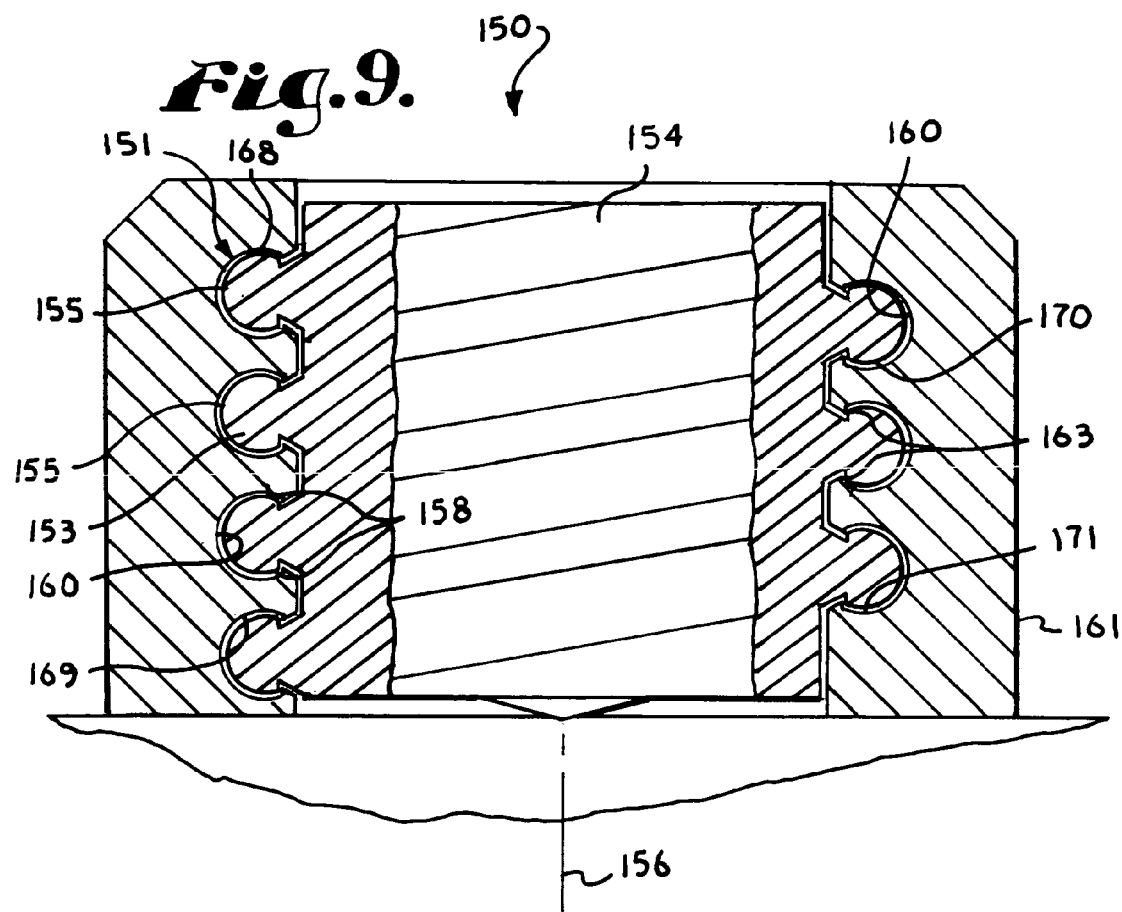
FIG. 9 is a view similar to FIG. 4 and illustrates details of a fifth modified bone screw and closure showing a radial bead embodiment of an interlocking form of the present invention.

FIG. 9 illustrates a radial bead embodiment of an implant 150 having a guide and advancement structure 151. The structure 151 includes a rounded external and bead interlocking form 153 projecting radially from a base 154 and forming a crest 155. The bead interlocking form 153 has a pair of splay resisting surfaces 158 facing generally toward an axis 156 of rotation of the base 154. A complementary groove internal interlocking form 160 is part of a screw head 161. The head interlocking form 160 has a pair of splay resisting surfaces 163 facing generally away from the axis 156. The structure 151 has the splay resisting surfaces 158 and 163 on thrust surfaces 168 and 169 respectively of the interlocking forms 153 and 160, as well as on clearance surfaces 170 and 171 thereof. The illustrated radial bead interlocking form 150 is, in some ways, a double sided variation of the rounded axial bead interlocking form of an earlier embodiment.

Figure 10:
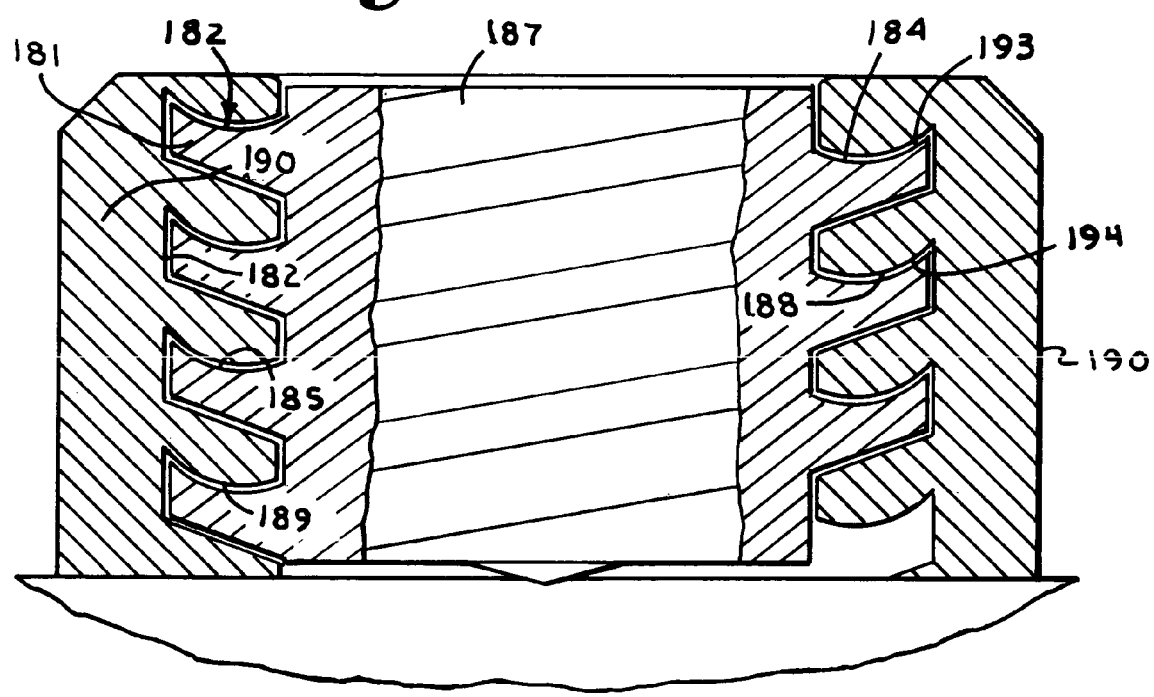
FIG. 10 is a view similar to FIG. 4 and illustrates details of a sixth modified bone screw and closure showing a scalloped depression or scooped embodiment of an interlocking form of the present invention.

FIGS. 10 and 11 illustrate a scalloped or scooped embodiment structure 180 including a pair of compound interlocking forms 181 and 182 according to the present invention. The interlocking form 181 is scalloped and, in effect, an inversion of the shallow rounded bead interlocking form similar to that of an earlier embodiment. The interlocking form 182 includes a shallow groove 184 formed in a thrust surface 185 of the external interlocking form 181 of a base 187 and a shallow bead 188 formed on a thrust surface 189 of the interlocking form 182 of a screw head 190. The groove 184 has a splay resisting surface 193 which cooperates with a complementary splay resisting surface 194 of the bead 188.

Illustrated in FIG. 12 is another guide and advancement structure 200 associated with a receiver member 201 and a closure member, such as a plug, 202 that is rotated into the receiver member 201. The structure 200 includes a first interlocking form 205 and a second interlocking form 206 attached to the closure member 202 and receiver member 201 respectively.

The first interlocking form 205 includes an arcuate upper surface 207 with a gripping or locking section 208. The second interlocking form 206 includes an arcuate lower surface 209 with a gripping or locking section 210. The interlocking forms 205 and 206 also have respective lower or leading surfaces 214 and 215 respectively that are sufficiently spaced to allow rotation about the axis thereof, but sufficiently close to be snug and not allow substantial movement of the forms 205 and 206 relative to each other in an axial direction without rotation.

FIG. 13 shows an alternative flange shaped embodiment of a guide and advancement structure 230 in accordance with the invention. The structure 230 is mounted on a closure 231 and a receiver 232 so that interlocking forms 233 and 234, which are seen in cross section, are helically mounted on the closure 231 and receiver 232 respectively.

The first interlocking form 233 is L or flange-shaped in cross section with a vertically or axially extending foot portion 240 with a gripping surface 241. The second interlocking form 234 generally complements the first and is also L or flange shaped except that a foot 243 thereof is much wider than the foot portion 240. The foot 243 has a gripping or wraparound surface 245 that abuts the surface 241 during assembly and resist radial movement between the receiver 232 and the closure 231.

Shown in FIG. 14 is another embodiment of a guide and advancement structure 260 in accordance with the invention. The structure 260 is utilized with a receiver 261 and a closure or plug 262. The structure 260 has first and second interlocking forms 263 and 264. The first interlocking form has an elongate wall 268 with a circular bead 269 attached to an end thereof opposite the closure 262. The bead 269 has opposed gripping surfaces 270 and 271. The second interlocking form 264 is shaped to mate with an generally surround the first interlocking form 263 except sufficient clearance is provided to allow the closure 262 to be rotated and advanced into the receiver 263 by sliding tangentially, but not radially. The second interlocking form 264 has a circular cross section channel 270 that receives the bead 269 and a pair of gripping surfaces 273 and 274 that engage and abut against the bead surfaces 270 and 271.

It is foreseen in accordance with the invention that certain regions of the interlocking forms may be eased or removed to allow for easier use which still maintaining the primary objective of resisting radial movement between the closure plug and the opposed arms of the bone screw to prevent splaying of such arms.

It is also seen in accordance with the invention that the axial aligned extension or depression on the described interlocking forms could in some cases be multiple in nature or formed by an undulating pattern.

It is to be understood that while certain forms of the present invention have been illustrated and described herein, it is not to be limited to the specific forms or arrangement of parts described and shown.

What is claimed and desired to be secured by Letters Patent is as follows:

1. An apparatus comprising:
   (a) a pair of spaced members, each having a top surface and a central vertical axis that are susceptible to splaying relative to one another away from the axis; each of said members including a first helical wound interlocking form with a top-facing outwardly extending linear surface and an opposite down-facing outwardly extending non-linear surface following a discontinuous helically wound path, the non-linear surface having a first portion extending from a root to a medial location and a second portion extending from the medial portion to a crest with the second portion sloping upwardly from the medial location to the crest;
   (b) a closure having a body and with a second helical wound interlocking form with a mating non-linear surface extending radially from said body; and
   (c) at least one of the first and second forms having a lip projecting axially therefrom at a location spaced from the associated closure members such that the one of the first and second forms is thickest in the region of the lip and the other of the first and second forms includes a groove; said lip and groove of said first and second forms being mateable by rotation and helical wound advancement of said closure relative to said members such that the non-linear surfaces mate so as to radially interlock said first and second forms to resist splaying of the spaced members.

2. The apparatus according to claim 1 wherein the linear surface and the non-linear surface second portion diverge from one another away from the root.

* * * * *

UNITED STATES PATENT AND TRADEMARK OFFICE
CERTIFICATE OF CORRECTION

PATENT NO. : 8,273,109 B2  
APPLICATION NO. : 10/831919  
DATED : September 25, 2012  
INVENTOR(S) : Roger P. Jackson Page 1 of 1

It is certified that error appears in the above-identified patent and that said Letters Patent is hereby corrected as shown below:

In the Claims

Column 16, line 10, in Claim 1, after "closure" insert --and--.

Signed and Sealed this
Seventh Day of May, 2013

Teresa Stanek Rea
*Acting Director of the United States Patent and Trademark Office*